United States Patent
Greenberg et al.

(10) Patent No.: US 9,005,267 B2
(45) Date of Patent: Apr. 14, 2015

(54) ROTATIONAL ALIGNMENT WIRE SYSTEM FOR AN ENDOVASCULAR DELIVERY SYSTEM

(75) Inventors: Roy K. Greenberg, Bratenahl, OH (US); Karl J. West, Geneva, OH (US); Vikash Ravi Goel, Cleveland Heights, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/454,821

(22) Filed: Apr. 24, 2012

(65) Prior Publication Data

US 2012/0323299 A1    Dec. 20, 2012

Related U.S. Application Data

(60) Provisional application No. 61/480,878, filed on Apr. 29, 2011.

(51) Int. Cl.
| | |
|---|---|
| *A61F 2/95* | (2013.01) |
| *A61F 2/07* | (2013.01) |
| *A61B 19/00* | (2006.01) |
| *A61F 2/954* | (2013.01) |
| *A61B 17/22* | (2006.01) |
| *A61F 2/89* | (2013.01) |

(52) U.S. Cl.
CPC .............. *A61F 2/07* (2013.01); *A61B 19/5244* (2013.01); *A61F 2/954* (2013.01); *A61B 2017/22038* (2013.01); *A61B 2019/4857* (2013.01); *A61B 2019/5253* (2013.01); *A61F 2002/9511* (2013.01); *A61F 2/89* (2013.01)

(58) Field of Classification Search
CPC .................................. A61F 2/95; A61F 2/954
USPC ............. 623/1.11, 1.12; 604/164.13; 600/109
See application file for complete search history.

(56) References Cited

U.S. PATENT DOCUMENTS

| | | | |
|---|---|---|---|
| 6,579,311 B1 | 6/2003 | Makower | |
| 6,592,526 B1 | 7/2003 | Lenker | |
| 7,232,459 B2 | 6/2007 | Greenberg et al. | 623/1.13 |
| 7,407,509 B2 | 8/2008 | Greenberg et al. | 623/1.35 |
| 7,611,529 B2 | 11/2009 | Greenberg et al. | 623/1.11 |
| 2004/0054403 A1* | 3/2004 | Israel | 623/1.35 |

(Continued)

FOREIGN PATENT DOCUMENTS

| | | |
|---|---|---|
| EP | 1 943 974 A1 | 7/2008 |
| EP | 2 085 108 A2 | 8/2009 |

(Continued)

OTHER PUBLICATIONS

Patent Examination Report No. 1, issued in Australian Patent Application No. 2012202484, dated Mar. 13, 2013, 4 pages.

(Continued)

*Primary Examiner* — Ryan Severson
*Assistant Examiner* — Anh Dang
(74) *Attorney, Agent, or Firm* — Brinks Gilson & Lione

(57) ABSTRACT

An endovascular delivery system includes an endovascular prosthetic device and a signal active guide wire engaging the endovascular prosthetic device. A rotary encoder is coupled with the guide wire and the endovascular prosthetic device to provide an encoder signal on the guide wire. The encoder signal is indicative of axial angular position of the endovascular prosthetic device during implantation of the endovascular prosthetic device in a body of a patient.

14 Claims, 5 Drawing Sheets

(56) References Cited

U.S. PATENT DOCUMENTS

| | | | |
|---|---|---|---|
| 2006/0004433 A1 | 1/2006 | Greenberg et al. | 623/1.11 |
| 2006/0276883 A1 | 12/2006 | Greenberg et al. | 623/1.31 |
| 2007/0100415 A1 | 5/2007 | Licata et al. | |
| 2007/0123910 A1 | 5/2007 | Hartley et al. | 606/108 |
| 2007/0270650 A1 | 11/2007 | Eno et al. | 600/145 |
| 2007/0276461 A1 | 11/2007 | Andreas et al. | |
| 2008/0139915 A1 | 6/2008 | Dolan et al. | |
| 2008/0177139 A1* | 7/2008 | Courtney et al. | 600/109 |
| 2008/0188921 A1 | 8/2008 | Yamasaki et al. | |
| 2009/0048663 A1 | 2/2009 | Greenberg | 623/1.35 |
| 2009/0179632 A1 | 7/2009 | Nishiguchi et al. | 324/207.25 |
| 2009/0222078 A1 | 9/2009 | Greenberg | 623/1.13 |
| 2010/0268204 A1 | 10/2010 | Tieu et al. | |
| 2010/0280363 A1 | 11/2010 | Skarda et al. | 600/424 |

FOREIGN PATENT DOCUMENTS

| | | |
|---|---|---|
| WO | WO 2007/058872 A2 | 5/2007 |
| WO | WO 2008/091409 A1 | 7/2008 |
| WO | WO 2010/056302 A2 | 5/2010 |

OTHER PUBLICATIONS

Patent Examination Report No. 1, issued in Australian Patent Application No. 2012202482, dated Feb. 27, 2013, 3 pages.

European Search Report in European Patent Application No. 12275050.8, document No. EP 2 517 677, published Oct. 31, 2012, 20 pages.

European Search Report in European Patent Application No. 12275051.6, document n No. EP 2 517 665 A1, published Oct. 31, 2012, 20 pages.

* cited by examiner

ROTATIONAL ALIGNMENT WIRE SYSTEM FOR AN ENDOVASCULAR DELIVERY SYSTEM

CROSS REFERENCE TO RELATED APPLICATIONS

This application claims priority under 35 U.S.C. §119(e) to U.S. provisional application No. 61/480,878, filed on Apr. 29, 2011, which application is incorporated herein in its entirety by this reference.

TECHNICAL FIELD

The present invention relates generally to a medical device. More particularly, the present invention relates to a rotational alignment wire system for an endovascular delivery system.

BACKGROUND

Throughout this specification, when discussing the application of this invention to the aorta or other blood vessels, the term "distal", with respect to a prosthesis, is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. In Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurismal, or ruptured vessels involves the use of a prosthetic device to provide some or all of the functionality of the original, healthy vessel, and/or preserve any remaining vascular integrity by replacing a length of the existing vessel wall that spans the site of vessel failure. One such prosthetic device is a stent graft. Stent grafts are used for treatment of vasculature in the human or animal body to bypass a repair or defect in the vasculature.

A length of a vessel which is treatable by such a prosthesis may have one or more branch vessels, i.e. vessels anastomosed to the main vessel. The celiac artery, superior mesenteric artery, left common carotid artery, and renal arteries, for example, are branch vessels of the aorta; the hypogastric artery is a branch vessel of the common iliac artery. Thus, a stent graft may be used to span an aneurism which has occurred in or is associated with the primary artery. Bypassing such a branch vessel without providing blood flow into it can cause problems and hence it has been proposed to provide a fenestration or a side branch on a stent graft which when deployed is positioned over the opening to the primary artery and then another stent graft can be deployed through the fenestration or side branch into the secondary artery to provide a blood flow path to the secondary artery.

When treating a vessel with a prosthetic device, it is therefore preferable to preserve the original circulation by providing a prosthetic branch that extends from the prosthesis to a branch vessel so that the blood flow into the branch vessel is not impeded. For example, the aortic section of one abdominal aortic prosthesis can be designed to extend above the renal arteries and to have prosthetic branches that extend into the renal arteries. Branch extension prosthetic modules ("branch extensions") can form a tromboning connection to the prosthetic branch to complete the prosthesis. Furthermore, some aneurysms extend into the branch vessels themselves. Deploying prosthetic branches and branch extensions into these vessels may help prevent expansion and/or rupture of these extended aneurysms.

Another example of a vessel that may be treated with a stent graft is the aortic arch. Aortic arch stent grafts are used in treating dissection and aneurismal dilation of the aortic arch. As with other primary vessels, many of these grafts have branches that maintain the patency of the branch arteries originating in the aortic arch. These branch arteries include the innominate artery, the left common carotid artery, and the left subclavian artery. A stent graft in the aortic arch may itself be branched to help direct the flow of blood into these branch arteries. Many of these branched grafts have branches that project outward from the prosthesis. Implanting the stent grafts in the branch arteries provides a challenge to surgeons because of the anatomic features of the aortic arch. Blood flow from the branch arteries must not be interrupted for an extended length of time because the branch arteries supply blood to the brain. Implanting branch stents that mate with the branches presents challenges because the natural orientation of the aortic arch must be matched or simulated by the stent grafts.

A surgeon may access the aortic arch through the branch arteries to implant small vessel stents. Guide wires are used to link the small vessel stents in the branch arteries with the branches of the aortic arch stent. However, much time may be lost in threading the guide wires through the openings of the aortic arch stent branches and through the branch arteries. A surgeon will often manipulate the guide wire around the difficult angles in the aortic arch stent channels before being able to connect with the delivery catheter of the branched stent.

In general, manipulating guide wires to correctly and reliably position a medical device such as a stent graft requires the surgeon's utmost skill and experience. The surgeon has relatively little information available defining where the medical device is positioned, its orientation and alignment. Conventionally, fluoroscopy has been used by surgeons to obtain real-time moving images of a patient's anatomy. However, the use of x-rays for fluoroscopy poses a health risk to the patient, the surgeon and other medical personnel. Because of small geometries, placement accuracy can be critical, particularly when positioning a device such as a stent graft in relation to another vessel such as a branch artery. There is therefore a need for an improved method and device for providing information to the surgeon about the position and orientation of the medical device. Moreover, there is a need for doing so using safer techniques that reduce the use of fluoroscopy.

BRIEF SUMMARY

In a first aspect, the present disclosure provides an endovascular delivery system. The endovascular delivery system includes an endovascular prosthetic device and a signal active guide wire engaging the endovascular prosthetic device. The delivery system further includes a rotary encoder coupled with the guide wire and the endovascular prosthetic device to provide an encoder signal on the guide wire. The encoder signal is indicative of axial angular position of the endovascular prosthetic device during implantation of the endovascular prosthetic device in a body of a patient.

In a second aspect, the present disclosure provides a method for deploying an endovascular prosthetic device. The method includes extending a guide wire in the vasculature of a patient between an incision and a desired deployment location and transvascularly positioning the endovascular prosthetic device over the guide wire near the desired deployment location in the vasculature of the patient. The method further includes detecting an encoder signal indicative of position or orientation or both of the endovascular prosthetic devices relative to the desired deployment position and producing an image on a display device. The image shows in substantially real time the position or orientation or both of the endovascular prosthetic devices relative to the desired deployment position.

In a third aspect, the present disclosure provides an endovascular graft delivery system which includes an endovascular graft positionable in a human body. The delivery system further includes a guide wire over which the endovascular graft may be transvascularly positioned in the human body, the guide wire including a signal collecting array of sensors arranged circumferentially around the guide wire. The delivery system further includes a transmitting device disposed on the endovascular graft to selectively actuate one or more of the sensors of the signal collecting array to provide on the guide wire an indication of axial and/or rotational position of the endovascular graft about the guide wire and a connector coupled to the guide wire to receive the indication of the axial position of the endovascular graft. In some embodiments, the system may also include a display device configured for connection to the connector to receive the indication of the axial position and to provide a visual display of the axial position for viewing by a surgeon positioning the endovascular graft in the human body. The display device may include an imaging device, a data storage to store previously-collected tomography data for the human body and a processor coupled to the data storage and the connector and operative in response to data and instructions to produce on the imaging device a combined image of anatomy of the human body based on the tomography data and position of the endovascular graft based on the indication of the axial position.

DETAILED DESCRIPTION OF THE PRESENTLY PREFERRED EMBODIMENTS

Figure 1:
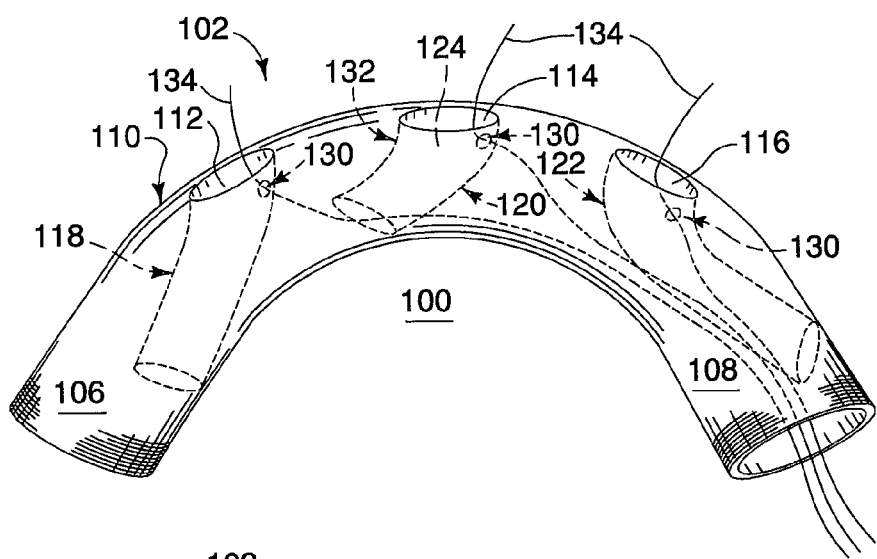
FIG. 1 shows a first embodiment of an endovascular prosthetic device.

The term "endoluminal" describes objects that are found or can be placed inside a lumen in the human or animal body. The term "endovascular" describes objects that are within a blood vessel. A lumen can be an existing lumen or a lumen created by surgical intervention. This includes lumens such as blood vessels, parts of the gastrointestinal tract, ducts such as bile ducts, parts of the respiratory system, etc. A "prosthetic device" is a prosthesis that can be placed inside one of these lumens.

The term "stent" means any device or structure that adds rigidity, expansion force, or support to a prosthesis. A Z-stent is a stent that has alternating struts and peaks (i.e., bends) and defines a generally cylindrical lumen. The "amplitude" of a Z-stent is the distance between two bends connected by a single strut. The "period" of a Z-stent is the total number of bends in the Z-stent divided by two, or the total number of struts divided by two.

The term "endoleak" refers to a leak around or through a prosthetic device. Endoleaks can occur through the fabric of a prosthesis, through the interconnections of a modular prosthesis, or around the ends of the prosthesis, inter alia. Endoleakage may result in the repressurizing of an aneurysm.

The term "branch vessel" refers to a vessel that branches off from a main vessel. Examples are the celiac and renal arteries which are branch vessels to the aorta (i.e., the main or primary vessel in this context). As another example, the hypogastric artery is a branch vessel to the common iliac, which is a main or primary vessel in this context. Thus, it should be seen that "branch vessel" and "main vessel" or "primary vessel" and "secondary vessel" are relative terms.

Some embodiments of the endovascular prosthetic system of the present invention include a prosthetic device having structural support. In some embodiments this structural support is a stent. In one embodiment, the stent may be formed by a plurality of discontinuous stent elements. In another embodiment, the stent may be formed from a single stent element. The stent may be located on the exterior of the device, the interior of the device, or both. The stent may be balloon-expandable or a self-expanding stent. Typically, the stent has a circular cross-section when fully expanded so as to conform to the generally circular cross-section of a body lumen. In one example, the stent may comprise struts and acute bends or apices that are arranged in a zigzag configuration in which the struts are set at angles to each other and are connected by the acute bends. The present invention can be used with a wide variety of stent configurations, including, but not limited to, shape memory alloy stents, expandable stents, and stents formed in situ. Preferably, the stent is formed from nitinol, stainless steel or another biocompatible metal or alloy, though any suitable material may be used.

The term "stent graft" refers to a type of endoluminal device made of a tubular graft material and supported by at least one stent. The stent graft material is preferably made of woven polyester having a twill weave and a porosity of about 350 ml/min/cm$^2$ (available, for example, from Vascutek Ltd., Renfrewshire, Scotland, UK). Any other suitable material may be used.

As noted, stent grafts may be either self-expanding or balloon-expandable, or they can have characteristics of both types of stent grafts. Self-expanding stent grafts may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

Referring now to the drawings, FIG. 1 shows a prosthetic device 100. The prosthetic device 100 is presented as exemplary only so as to illustrate generally the relevant structures and functions of a device with which the presently disclosed features may be used. These structures and functions may be used in conjunction with the widest variety of devices and the illustrated examples should not limit the extension of these structures and functions to other implementations.

The prosthetic device 100 has a primary prosthesis 102 including a major lumen 104 extending therethrough from the proximal end 106 to the distal end 108 of the primary prosthesis 102. The prosthetic device 100 has a major wall 110. The major wall 110 defines the major lumen 104 and occludes an aneurysm once deployed. First opening 112, second opening 114, and third opening 116 are shown in the major wall 110 that correspond to the first socket 118, second socket 120, and third socket 122 and to three branch arteries that branch away from the vessel in which the primary prosthesis 102 is deployed. Although the illustrated embodiment has three sockets, other embodiments of the present invention provide primary prostheses with one or two openings corresponding to one or two sockets. In other embodiments, there is at least one socket in the major wall 110. In yet other embodiments, the prosthetic device 100 has no sockets but features one or more fenestrations for purposes such as joining the prosthetic device to another prosthetic device to form a modular prosthesis. There are also embodiments wherein the primary prosthesis 102 further comprises a structural support around at least a portion of the major wall 110. The structural support may be a stent in some embodiments.

At least a portion of the first socket 118, second socket 120, and third socket 122 extend into the major lumen 110 from the openings 112, 114, and 116. While the first socket 118 and second socket 120 are angled in a proximal direction, the third socket 122 is angled in a distal direction in the figure shown. The sockets, therefore, are arranged in fluid communication with the major lumen 110. There may be other embodiments in which the sockets are angled in directions suitable for other specified treatments. The first socket 118, second socket 120, and third socket 122 mate with the proximal ends of secondary prostheses to form a secure seal with the primary prosthesis 102 at the openings. The sockets 118, 120, 122 are angled to receive the flow of blood and direct it through their minor lumens 124 into the branch arteries. The sockets 118, 120, 122 have fenestrations 130 that are in fluid communication with the minor lumens 124 and the major lumen 110. The fenestrations 130 are located in the distal side 108 of the minor walls 132 of the sockets, the portion that extends into the major lumen 110.

Although FIG. 1 illustrates an embodiment with three sockets 118, 120, 122, there are other embodiments comprising at least one socket or two sockets. In the embodiment illustrated, there is a first socket 118 and opening 112 configured to direct blood flow into the innominate artery when the prosthetic device 100 is positioned in the aortic arch of a human patient. The second socket 120 and opening 114 are configured to direct blood flow into the left common carotid artery when the prosthetic device 100 is positioned in the aortic arch of a human patient. The third socket 122 and opening 116 are configured to direct blood flow into the left subclavian artery when the prosthetic device 100 is positioned in the aortic arch of a human patient.

Guide wires 132 extend from the distal end 108 of the primary prosthesis 102 through the fenestrations 130 to extend into the minor lumens 124 of the sockets and out of the primary prosthesis 102 through the openings in the major wall 110. Because of their arrangement in the present invention, upon placement and deployment, the guide wires 134 will be positioned in the target vessels for snaring with a double lumen catheter or some other guide wire. The guide wires 134 can have angled tips, flexible tips, compliant tips, or blunt tips.

Figure 2:
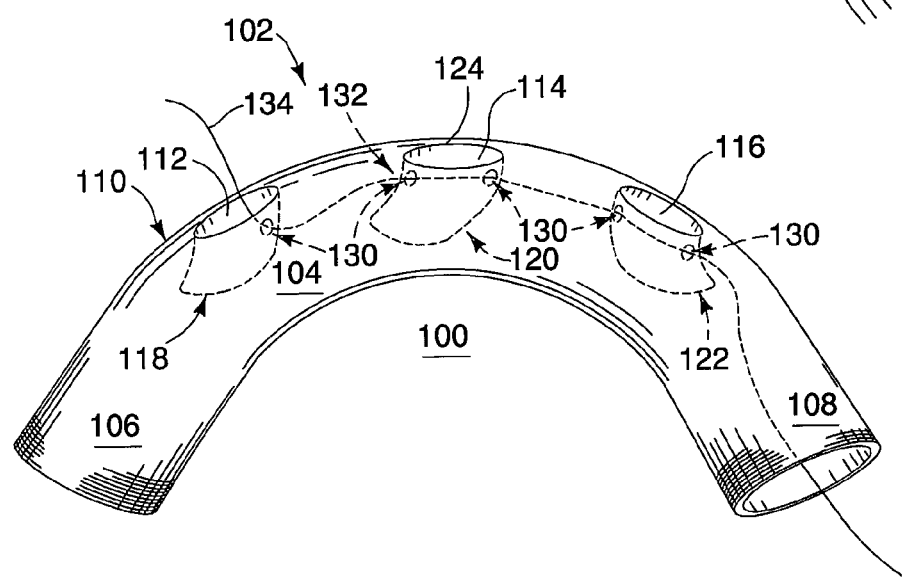
FIG. 2 shows a second embodiment of an endovascular prosthetic device.

FIG. 2 shows an embodiment having one guide wire 134 threaded through the fenestrations 130 of the first 118 socket, second socket 120 and third socket 122. Although the embodiment shown has two fenestrations 130 on the second socket 120 and third socket 122, there may also be embodiments having only one fenestration 130 per socket. The guide wire 134 is used to guide and deploy a secondary prosthesis, such as a side branch graft, into the first opening 112 of the first socket 118. After deployment of the first secondary prosthesis, the guide wire 134 is pulled out of the first socket 118 and into the second branch 120. In such an embodiment, the tip of the guide wire 134 preferably is formed of a shape memory alloy such as nitinol. This allows the tip of the guide wire 134 to assume an orientation pointing out of the second opening 124.

The fenestrations 130 in the branches do not hinder blood flow once the prosthesis 100 is properly deployed. Once a secondary prosthesis such as a tubular side branch graft prosthesis is positioned and deployed in a socket, the guide wire 134 is retracted from the fenestration 130. The proximal end of the secondary prosthesis occludes the fenestration 130 such that blood flow is not detrimentally affected.

The endovascular prosthetic device of FIGS. 1 and 2 can be deployed into the aortic arch of a human patient by methods known in the art. Generally, a primary prosthesis is introduced into an aortic arch having a aneurysm or other pathology. A main guide wire is inserted into the femoral artery (right or left) through an incision and is guided through the descending aorta, the aortic arch, and the ascending aorta. The main guide wire is guided to the aortic valve of the heart in some methods.

Subsequently, the primary prosthesis is partially expanded, for example by releasing constraints which form ties partially constraining the prosthesis. In the case of the device of FIG. 1 or of FIG. 2, first opening 112, second opening 114, and third opening 116 are aligned with the innominate artery, the left common carotid artery and the left subclavian artery, respectively. The guide wires are appropriately positioned in the arteries for snaring. Diagnostic imagining can be used to confirm the proper placement of all the elements. Conventionally, radiopaque markers can be placed to mark positions of the first opening 112, second opening 114 and third opening 116. Further, radiopaque markers can be placed at other locations on the primary prosthesis to assist in marking the position of the device. The prosthetic device is implanted and positioned using a suitable endovascular graft delivery system.

Figure 3:
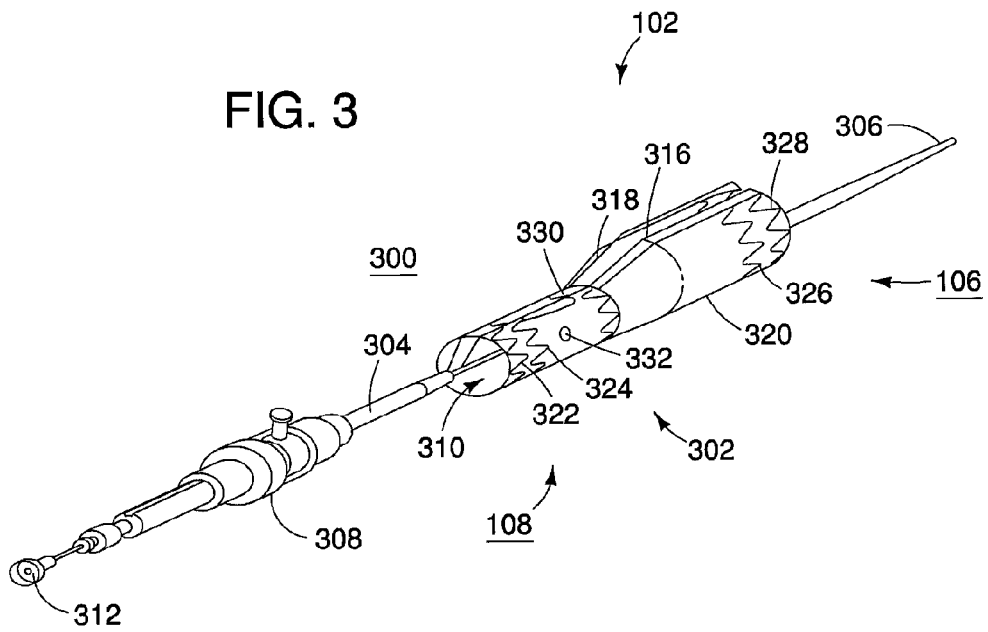
FIG. 3 shows a first view of endovascular prosthetic delivery system.

FIG. 3 shows an endovascular graft delivery system 300. The endovascular graft delivery system 300 includes an endovascular prosthetic device 302, a sheath 304, a proximal tapered nose cone dilator 306, a handle 308, a connector 312, a first trigger wire 316 and a second trigger wire 318. This embodiment is exemplary only. Alternative embodiments may include additional elements or may delete or modify some of the elements illustrated in FIG. 3. The endovascular graft delivery system 300 may be modified so as to be adapted to a particular purpose, function or anatomy. The endovascular graft delivery system 300 illustrated in FIG. 3 is particularly suited to deployment of an aortic stent graft to repair an aortic aneurysm in the ascending aorta, the descending aorta or the aortic arch of a human patient. Extensions to other applications will be apparent.

The endovascular prosthetic device 302 in the illustrated embodiment is an aortic stent graft. The endovascular prosthetic device 302 includes a tubular body 320 made of a biocompatible graft material and at least one stent. The endovascular prosthetic device 302 may be formed from a single material, a blend of materials, a weave, a laminate or a composite or two or more materials. The tubular body 320 defines a major lumen 310. The tubular body 320 may be shaped to accommodate particular anatomical configurations. For example, the tubular body 320 may define one or more openings similar to openings 112, 114, 116 in the prosthesis 102 of FIG. 1. Such openings may be adapted to form minor lumens with branch grafts that are surgically implanted along with the endovascular prosthetic device 302. As will be appreciated by those of ordinary skill, the particular material and configuration, including openings and shape, of the endovascular prosthetic device 302 may be adapted in any suitably manner to fulfill particular requirements.

In the exemplary embodiment, the endovascular prosthetic device 302 includes first stent 322, second stent 324, third sent 326 and fourth stent 328. The stents 322, 324, 326, 328 may be of any configuration. In the exemplary embodiment, Z-stents are used. A Z-stent is a stent that has alternating struts and peaks (i.e., bends) and defines a generally cylindrical lumen. The stents 322, 324, 326, 328 may be balloon expandable or self-expanding. The stents have a circular cross-section when fully expanded so as to conform to the generally circular cross-section of a body lumen such as the aorta of the human body.

The endovascular prosthetic device 302 further includes a fenestration 332. The fenestration 332 may be located in any suitable location and be used for any suitable purpose during deployment and subsequent use of the endovascular prosthetic device 302.

The sheath 304 is generally coaxial with the endovascular prosthetic device 302. The sheath 304 is slideable between two positions. Prior to and during implantation of the endovascular prosthetic device 302, the sheath 304 is in an initial proximal position with the undeployed endovascular prosthetic device 302 contained within the sheath 304. During this time, the delivery system 300 including the endovascular prosthetic device 302 may be introduced into the vasculature of a patient such as through an incision to access an iliac artery of the patient. When the endovascular prosthetic device 302 is properly positioned, the sheath 304 may be retracted to the position shown in FIG. 3 and the endovascular prosthetic device 302 deployed.

The proximal tapered nose cone dilator 306 forms the leading edge of the delivery system 300. The proximal end of the dilator 306 is tapered for accessing and dilating a vascular access site over a guide wire, such as the guide wires 134 of FIGS. 1 and 2. Such as guide wire is inserted in a vessel with an introducer needle. The guide wire may be maneuvered into position at a desired vascular location. The dilator 306 may then be maneuvered into position over the guide wire.

The handle 308 provides control of delivery system 300 during deployment of the endovascular prosthetic device 302. The handle 308 includes dilator control for sliding the dilator between the distal and proximal positions during deployment. The handle 308 includes trigger wire release arrangements 334 for releasing the trigger wires 316, 318, as will be discussed in further detail below.

The connector 312 permits mechanical connection to other equipment such as syringes and other medical apparatus. In that regard, a standardized connector may be used so that a wide variety of apparatus can be quickly and reliably coupled with the delivery system 300. An exemplary connector is a Luer-Lok® connector hub. Any other suitable connector system may be provided for mechanical or fluidic connection to other equipment. In addition to the connector 312 for mechanical connection and fluidic communication, the connector 312 may include an electrical connector or an optical connector.

The trigger wires 316, 318 selectively provide mechanical, electrical and optical control of the endovascular graft delivery system 300. The endovascular prosthetic device 302 includes mechanical constraints of the type known in the art. The mechanical constraints can be selectively released by activating one or more of the trigger wires. The mechanical constraints maintain the endovascular prosthetic device 302 in a fully or partially collapsed configuration prior to and during deployment of the endovascular prosthetic device 302. In the collapsed configuration, the endovascular prosthetic device 302 is sufficiently small to be introduced into the vascular system to the desired deployment location. When properly located, for example, at the site of an aortic aneurysm, the trigger wires may be selectively activated to thereby release the constraints. Under force of stents 322, 324, 326, 328 or other device such as a balloon, the endovascular prosthetic device 302 expands to fill the vascular space.

In FIG. 3, the proximal end of the stent graft is shown fully deployed and the distal end of the stent graft is shown partially deployed. In many applications, two or more trigger wires attach the stent graft proximally and one trigger wire attaches the stent graft distally, although only two proximal trigger wires are illustrated in the drawing figure. Also, while the drawing figure shows the trigger wires 316, 318 disposed on the outside of the endovascular prosthetic device 302, one or more of the trigger wires 316, 318 may be disposed on the inside, in the lumen 310. The number and location of trigger wires and their arrangement may be tailored to the particular application for which the endovascular prosthetic device 302 is intended.

Figure 4:
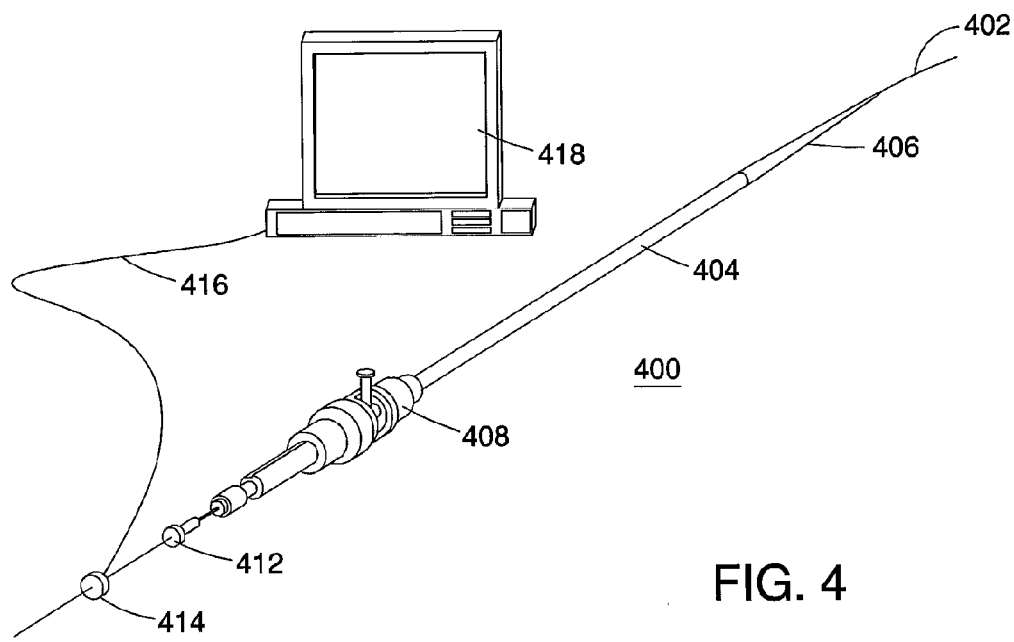
FIG. 4 shows a second view of an endovascular prosthetic device delivery system.

FIG. 4 shows a second view of a delivery system 400 for an endovascular prosthetic device. The delivery system 400 is particularly well adapted for resolving the axial and angular position of a branched endograft in vivo and providing visual feedback to an end user such as a surgeon via a computer. The delivery system 400 includes a guide wire 402, a sheath 404, a dilator 406, a handle 408 and a connector 412. The delivery system 400 in the illustrated embodiment further includes computer interface 414, computer interface cable 416 and data processing system 418. Particular embodiments may include more or fewer elements, and some elements may be substituted for those shown in FIG. 4. For example, the guide wire 402, a sheath 404, a dilator 406, a handle 408 and a connector 412 may be packaged and sold together as an introducer or other arrangement in which the introducer is intended to be used a single time during implantation surgery for a single patient. The computer interface cable 414 and data processing system 418 may be reused with a variety of introducers or other elements.

The guide wire 402 may be introduced in the body of a patient by means of an incision providing access to the vasculature of the patient. For example, by means of an incision in the femoral artery, the guide wire 402 may be introduced and directed to the descending aorta, the aortic arch and the ascending aorta of the patient. The dilator 406 engages the guide wire 402 and slides over the guide wire 402 through the vasculature of the patient to the vicinity of the desired deployment location. The dilator 406 contains an endovascular prosthetic device such as an aortic stent graft. When properly positioned at the desired deployment location, the endovascular prosthetic device may be deployed and the dilator 406 withdrawn from the patient. The sheath 404 and the handle 408 permit grasping and manipulation of the delivery system 400 by a surgeon during the procedure. The connector 412 permits fluidic, mechanical and possibly electrical and optical connection between the delivery system and other components.

As will be described in greater detail below in conjunction with FIGS. 5, 6, 7 and 8, the guide wire 402 is signal-active and permits display of positioning information on the data processing system 418. The guide wire 402 conveys an encoder signal to the computer interface 414. Toward that end, the computer interface 414 is adapted to make electrical or optical connection between the guide wire 402 and the computer interface cable 416 and, in turn, the data processing system 418. The computer interface 414 may be any conventional or specialized connection device for making electrical or optical connection to the guide wire 402.

The data processing system 418 may be any suitable data processing system. The data processing system 418 accordingly includes a processor and memory or other data storage and a display device. The data processing system 418 is responsive to the encoder signal received from the computer interface 414 to produce a visual image illustrating alignment of the endovascular prosthetic device with a desired deployment location in the body of the patient. The memory of the data processing system 418 is configured to store tomography data based on the anatomy of the patient. For example, in preparation for implantation of the endovascular prosthetic device, a series of computerized tomography (CT) scans may be taken of the patient and stored as computer readable data in the memory of the data processing system 418. The processor of the data processing system 418 is then operative in response to the tomography data and instructions stored in the memory to produce on the display device a composite image showing orientation of the endovascular prosthetic device relative to anatomy of the patient. The image is thus a combined image of anatomy of the human body based on the tomography data and position of an endovascular graft or other endovascular prosthetic device based on the indication of the axial position of the endovascular graft.

Figure 6:
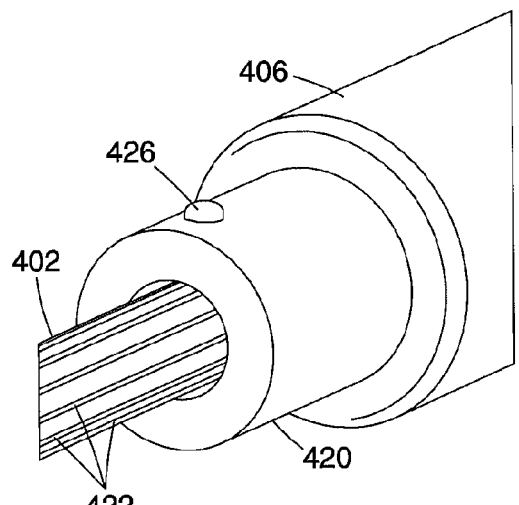
FIG. 6 shows a detailed orthographic view of a portion of the endovascular prosthetic device delivery system of FIG. 4.
Figure 5:
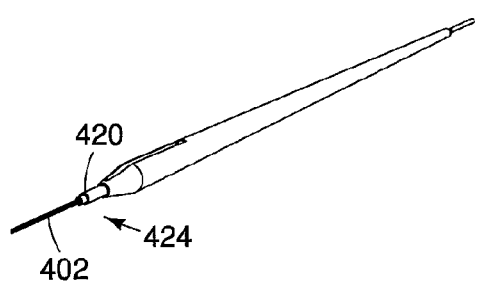
FIG. 5 shows an orthographic view of a portion of the endovascular prosthetic device delivery system of FIG. 4.
Figure 8:
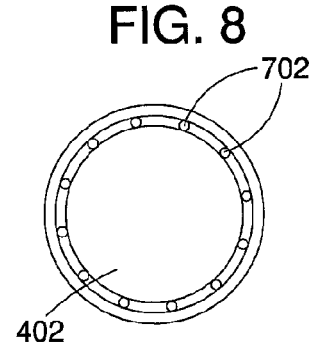
FIG. 8 shows a different detailed end view of a portion of the endovascular prosthetic device delivery system of FIG. 4.

The guide wire 402 may include one or more electrical conductors or optical fibers for conveying signals to the computer interface 414. FIG. 5 shows an orthographic view of a portion of the endovascular prosthetic device delivery system of FIG. 4. FIG. 6 shows a detailed orthographic view of a portion of the endovascular prosthetic device delivery system of FIG. 4. FIGS. 5 and 6 show the guide wire 402 engaging the proximal end 424 of the dilator 406. The proximal end 424 includes a collar 420, a transmitter or other electronic device 426. The guide wire 402 may include a single conductor or as shown in FIG. 8, a bundle of conductors 422. The conductors 422 may include electrical conductors or optical fibers or both. The transmitter 426 may be any device such as a magnet or an electrically active or passive electronic device and is attached at a prescribed location.

Figure 7:
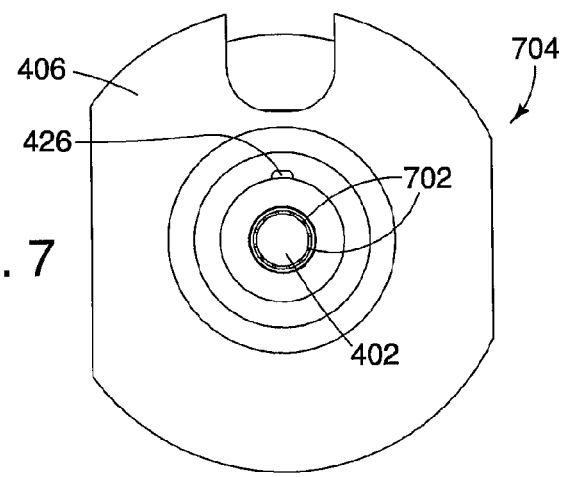
FIG. 7 shows a detailed end view of a portion of the endovascular prosthetic device delivery system of FIG. 4.

FIG. 5 shows a detailed end view of a portion of the endovascular prosthetic device delivery system 400 of FIG. 4. FIG. 6 shows a different detailed end view of a portion of the endovascular prosthetic device delivery system 400 of FIG. 4. FIGS. 7 and 8 show a cross section view of the guide wire 402. The guide wire 402 includes a signal collecting array 702 of elements disposed circumferentially around the guide wire 402. Any number of elements may be disposed on the guide wire 402, from 2 to a substantially infinite number. Including more elements will increase the precision of measurement.

The transmitter 426 in combination with the signal collecting array of elements 702 forms a rotary encoder 704. The rotary encoder 704 is coupled with the guide wire 402 and the endovascular prosthetic device to provide an encoder signal on the guide wire 402. The encoder signal is indicative of axial angular position of the endovascular prosthetic device during implantation of the endovascular prosthetic device in a body of a patient. Rotating the dilator 406 with the sensor 402 about the guide wire 402 produces the encoder signal on the guide wire 402. The encoder signal is related to the relative axial position of the endovascular prosthetic device and the dilator 406 about the wire. As the surgeon rotates the delivery system 400 to position the endovascular prosthetic device, the encoder signal will vary substantially in real time. The encoder signal is provided to the computer interface 414 and thus to the computer interface cable 416. The encoder signal may then by sensed and processed by the data processing system 418.

Figure 9:
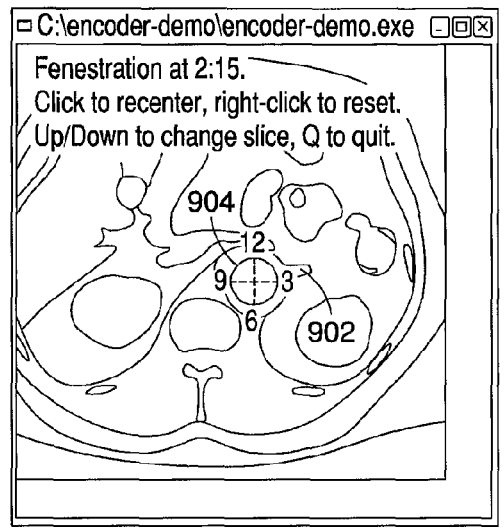
FIG. 9 shows a display image produced by the endovascular prosthetic device delivery system of FIG. 4.

FIG. 9 shows a display image produced by the endovascular prosthetic device delivery system of FIG. 4. In use, the endovascular delivery system of FIG. 4 is placed over the guide wire 402 which in this embodiment forms an active signal wire. Under fluoroscopy, the prosthetic device is positioned in its correct longitudinal position. The transmitter 426 cooperates with the array 702 of elements to encode the rotary or axial orientation of the prosthetic device.

After the prosthetic device and delivery system 400 are placed longitudinally, the data processing system 418 is attached to the end of the signal wire 402, for example using the computer interface 414 and computer interface cable 416. This establishes communication between the data processing system and the signal wire or guide wire 402. The surgeon performing the procedure may access the memory of the data processing system 418 to scan through CT images for the appropriate image showing the target blood vessel with the desired deployment location. The surgeon then zeroes the longitudinal and axial positions of the prosthetic device and the encoder wire system. The data processing system 418, using instructions and data stored in memory plus the CT data and the encoder signal, implements an alignment algorithm.

The rotational position of the prosthetic device and the delivery system 400 can be visually tracked on the display device of the data processing system by the alignment algorithm, as illustrated in FIG. 9. By aligning the visual marker 902 with a target artery 904, a fenestration in the prosthetic device or a branch device can be properly oriented for device deployment.

Figure 10:
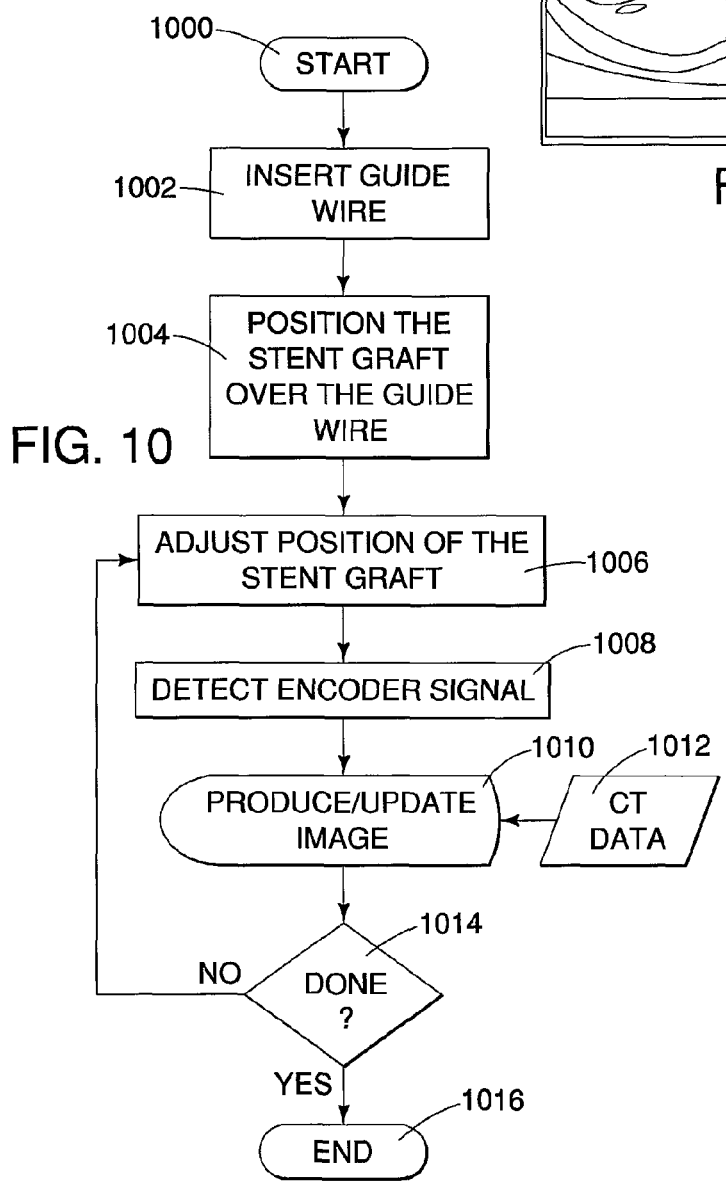
FIG. 10 is a flow diagram illustrating a method for deploying an endovascular prosthetic device.

FIG. 10 is a flow diagram illustrating a method for deploying an endovascular prosthetic device. The method begins at block 1000. At block 1002, a guide wire is inserted to initiate the implantation procedure. In some embodiments, the guide wire includes a signal active wire configured to convey an encoder signal from a rotary encoder. The guide wire may include one or more electrical conductors or one or more optical fibers for conveying the encoder signal.

At block 1004, a stent graft or other endovascular prosthesis device is positioned over the guide wire. The guide wire is used to advance the stent graft toward the desired deployment location.

At block 1006, the position of the stent graft is adjusted. In particular, the axial position of the stent graft is adjusted to align features such as fenestrations or branch vessel appendages with branch vessels. At block 1008, the encoder signal produced by the rotary encoder is detected, for example at a data processing system. At block 1010, an image is produced by the data processing system. In one embodiment, the image is produced as a composite of the encoder signal and computerized tomography (CT) data 1012.

At block 1014, it is determined if the process is complete. That is, the positioning of the stent graft is verified. This process may rely on the surgeon's experience and judgment. Alternatively, or in addition, this process may employ quantitative measure obtained and processed using the encoder signal and the CT data. If the process is not complete, control returns to block 1006 to further adjust the stent graft. Alternatively, if the process is complete, the method ends at block 1016.

Figure 11:
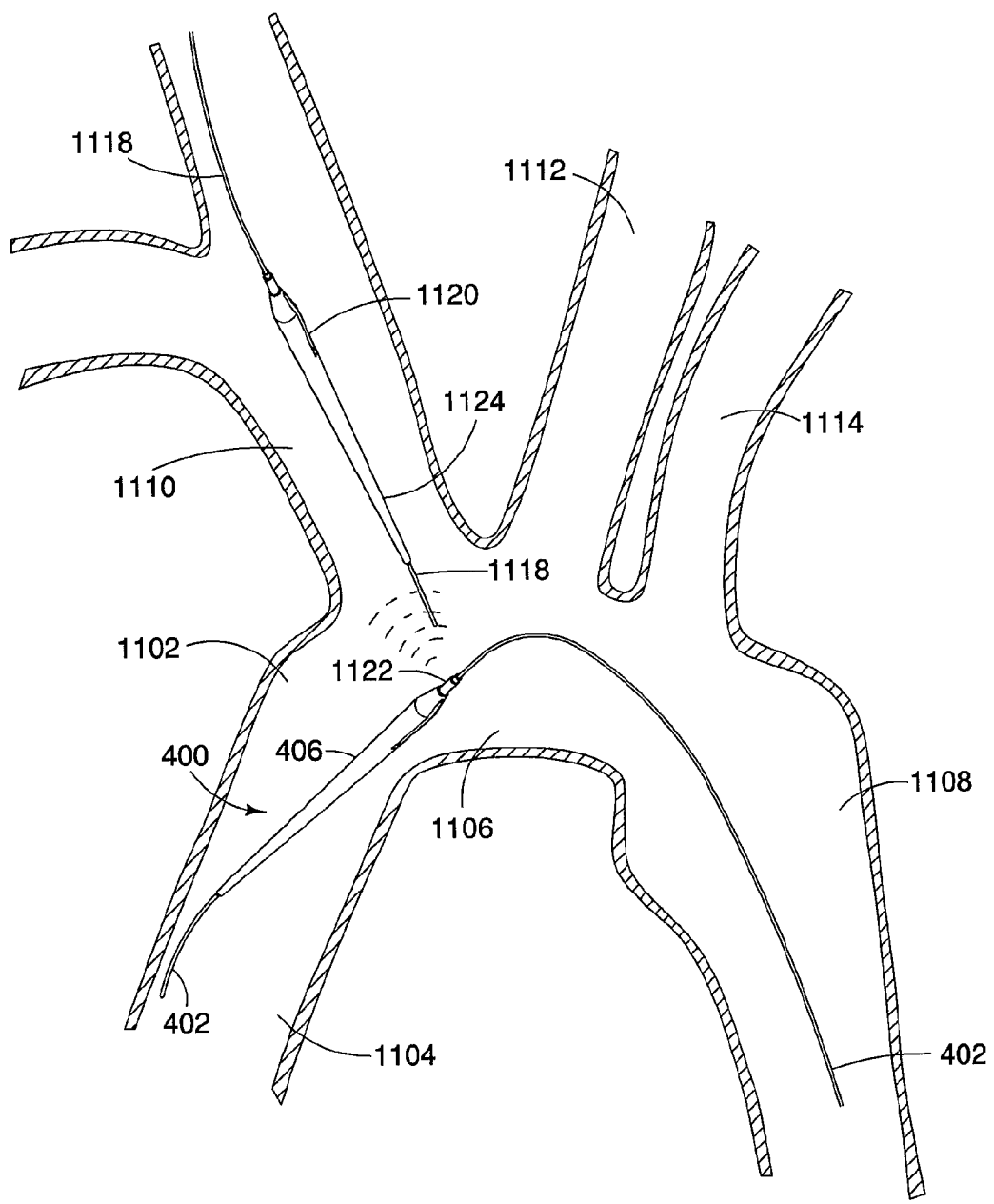
FIG. 11 illustrates deployment of an endovascular prosthetic device.

FIG. 11 illustrates deployment of an endovascular prosthetic device. The prosthetic device is delivered in a delivery system 400 including dilator 406. The dilator 406 and other structures containing the prosthetic device are extended along a guide wire 402 which has been disposed within the aorta 1102 of a patient. In FIG. 11, the aorta 1102 includes ascending aorta 1104, aortic arch 1106 and descending aorta 1108. The guide wire may be introduced to the vascular system of the patient for example at a femoral artery. Extending from the aortic arch 1106 are the innominate artery 1110, the left common carotid artery 1112 and the left subclavian artery 1114.

For positioning a prosthetic device such as the primary prosthesis 102 (FIG. 1) in the aortic arch 1106, the prosthetic device is contained within the delivery system including the dilator 406 as the delivery system is advanced along the guide wire 402. Proper positioning requires that fenestrations such as first opening 112, second opening 114, and third opening 116 (FIG. 1) must be aligned with the innominate artery 1110, the left common carotid artery 1112 and the left subclavian artery 1114, respectively. This means that the prosthetic device must be aligned longitudinally as well as rotationally.

To assist in alignment, the delivery system includes a transmitter 1122 positioned on the delivery system. The transmitter 1122 may be any sort of electrical, magnetic or optical device as described herein. Further, a secondary delivery system 1120 may be introduced in one or more of the innominate artery 1110, the left common carotid artery 1112 and the left subclavian artery 1114. The secondary delivery system 1120 in FIG. 11 is advanced along a secondary guide wire 1118 to a point such as is shown in FIG. 11 proximate the origin of the innominate artery 1110. The secondary delivery system 1120 cooperates with the transmitter 1122 or other electronic device of the delivery system 400 to position the prosthetic device.

The secondary delivery system 1120 may use any convenient design. In one example, the secondary delivery system 1120 deploys a secondary prosthesis which may be joined to a device such as primary prosthesis 102 shown in FIG. 1. When the primary prosthesis and the secondary prosthesis are implanted and deployed, they together form a unitary prosthesis for supplying blood from the aorta 1102 to the innominate artery 1110. One technique for a branched stent graft system is disclosed in US patent publication number 2009/0048663 A1 filed in the name of Roy K. Greenberg on Aug. 8, 2008, which is incorporated herein in its entirety. In another application, the secondary delivery system 1120 does not include a secondary prosthesis.

The secondary delivery system 1120 includes an electronic element 1124 which communicates with the electronic device 1122 of the delivery system. For example, as illustrated in FIG. 11, the electronic device 1122 may be a transmitter arranged to transmit an electromagnetic signal at a predetermined frequency or with a predetermined modulation or with any other suitable identifiable characteristics. In this example the electronic device 1124 of the secondary delivery system comprises a receiver configured to detect the specified frequency, modulation or other characteristics. For example, if the transmitter transmits at 400 KHz, the receiver is tuned to receive a 400 KHz signal.

The guide wire 402 may be used to power the electronic element or to provide an electrical, magnetic or optical signal to the electronic device 1122. The guide wire 402 may be a conductor such as a metal to convey the signal to the electronic device 1122. Similarly, the guide wire 1118 of the secondary delivery system 1120 may be used to convey received signal to a point external to the patient's body. It should be noted that the transmitter and receivers may be changed so that the electronic device 1122 of the delivery system is a receiver or otherwise is responsive to communication of information from the electronic device 1124 of the secondary delivery system 1120. While the guide wires 402, 1118 may be used for communication, a trigger wire may be used instead or in addition, where a trigger wire is connected to the prosthetic device to releasably deploy the prosthetic device upon accurate placement of the prosthetic device.

Relying on the cooperative communication between the electronic elements 1122 and 1124, the prosthetic device may be accurately positioned both longitudinally and rotationally. The electronic devices 1122, 1124 may be chosen or designed to permit this. For example, one electronic device may include a receiver responsive to radio signals transmitted by the other electronic device. The receiver may produce a received signal strength indication (RSSI) signal. The RSSI signal indicates the relative strength of the radio signals detected by the receiver. RSSI circuits are well known in radio receiver design. As the transmitter and receiver move in relation to each other, the RSSI signal will provide an indication of the proximity of the transmitter and receiver. As the RSSI signal indicates a stronger received signal, that may indicate that the two components are moving closer. A weakening RSSI signal indicates the components are moving apart. The RSSI signal may be reported or processed to provide an indication of the positioning of the prosthetic device. A surgeon implanting the device may use the RSSI signal or other indication to conclude that the prosthetic device is correctly positioned and ready for deployment.

Further, additional electronic devices may be included to provide additional positioning information. For example, multiple electronic devices may be positioned along the delivery system 400 including the guide wire 402 and the dilator 406. In addition or instead, multiple electronic devices may be positioned in the left common carotid artery 1112 and/or the left subclavian artery 1114. By detecting communication of information between and among these electronic devices, a prosthetic device such as an aortic stent graft may be correctly positioned longitudinally and rotationally. This may be achieved without use of fluoroscopy or with limited use of fluoroscopy. While these techniques have been shown in relation to the aortic arch, the same techniques may be applied to any other body lumen as well.

From the foregoing, it can be seen that the present invention provides a method and apparatus for resolving the angular and longitudinal position of a branched endograft in vivo, providing visual feedback to the surgeon via a computer. The conventional guide wire of an endovascular prosthesis deployment system is modified to a signal active guide wire. The signal active guide wire cooperates with the delivery system to form a rotational encoder providing angular alignment of features such as graft fenestration or branch vessel appendages to their respective target by superimposing the data on an axial CT scan. Benefits include more accurate positioning of end grafts, particularly stent grafts in locations such as the aortic arch, and reduced irradiation by x-rays of fluoroscopy.

While particular embodiments of the present invention have been shown and described, modifications may be made. It is therefore intended that the foregoing detailed description be regarded as illustrative rather than limiting, and that it be understood that it is the following claims, including all equivalents, that are intended to define the spirit and scope of this invention.

The invention claimed is:

1. An endovascular delivery system comprising:
    an endovascular prosthetic device;
    a signal active guide wire engaging the endovascular prosthetic device; and
    a rotary encoder coupled with the guide wire and the endovascular prosthetic device to provide an encoder signal on the signal active guide wire, the encoder signal indicative of an axial angular position of the endovascular prosthetic device during implantation of the endovascular prosthetic device in a body of a patient, the rotary encoder including a device positioned on the endovascular prosthetic device and being rotatable with the endovascular prosthetic device about the signal active guide wire;
    a signal collecting array of elements disposed circumferentially around the signal active guide wire, the signal collecting array of elements being responsive to a position of respective selected elements of the signal collecting array of elements relative to the device to generate the encoder signal in the signal active guide wire as a time varying signal as the device is rotated relative to the signal collecting array of elements; and wherein the device of the rotary encoder further comprises
    a magnet fixed on the endovascular prosthetic device to cause the signal collecting array of elements disposed circumferentially around the signal active guide wire to generate the encoder signal on the guide wire in response to rotation of the endovascular prosthetic device, including the magnet, relative to the signal collecting array of elements disposed circumferentially around the signal active guide wire.

2. The endovascular delivery system of claim 1 further comprising a connector interface in signal communication with the signal active guide wire.

3. The endovascular delivery system of claim 2, wherein the connector interface is configured to produce digital data based on the encoder signal.

4. The endovascular delivery system of claim 3, wherein the connector interface comprises an optical interface to produce optical data on an optical fiber in response to the encoder signal.

5. The endovascular delivery system of claim 1, further comprising:
    a data processing system configured to be coupled with the signal active guide wire and selectively in communication with the rotary encoder and responsive to the encoder signal to produce a visual image illustrating alignment of the endovascular prosthetic device with a desired deployment location for the endovascular prosthetic device in the body of the patient.

6. The endovascular delivery system of claim 5, wherein the data processing system comprises:
    a display device;
    a memory configured to store tomography data based on an anatomy of the patient; and a processor in data communication with the memory and the rotary encoder, the processor operative in response to the encoder signal and data and instructions stored in the memory to produce on the display device a composite image showing an orientation of the endovascular prosthetic device relative to that anatomy of the patient.

7. The endovascular delivery system of claim 1, wherein the endovascular prosthetic device comprises an aortic stent graft.

8. An endovascular delivery system comprising:
    an endovascular prosthetic device;
    a signal active guide wire engating the endovascular prosthetic device; and
    a rotary encoder coupled with the signal active guide wire and the endovascular prosthetic device to provide an encoder signal on the signal active guide wire, the encoder signal indicative of an axial angular position of the endovascular prosthetic device during implantation of the endovascular prosthetic device in a body of a patient, the rotary encoder including a device positioned on the endovascular prosthetic device and being rotatable with the endovascular prosthetic device about the signal active guide wire;
    a signal collecting array of elements disposed circumferentially around the signal active guide wire, the signal collecting array of elements being responsive to a position of respective selected elements of the signal collecting array of elements relative to the device to generate the encoder signal in the signal active guide wire as a time varying signal as the device is rotated relative to the signal collecting array of elements; and wherein the device of the rotary encoder further comprises
    an electronic device positioned on the endovascular prosthetic device and being rotatable with the endovascular prosthetic device about the signal active guide wire, the electronic device being electromagnetically coupled with the respective selected elements of the signal collecting array to generate an electronic signal as the encoder signal in the guide wire.

9. The endovascular delivery system of claim 8, further comprising a connector interface in signal communication with the signal active guide wire.

10. The endovascular delivery system of claim 9, wherein the connector interface is configured to produce digital data based on the encoder signal.

11. The endovascular delivery system of claim 10, wherein the connector interface comprises an optical interface to produce optical data on an optical fiber in response to the encoder signal.

12. The endovascular delivery system of claim 8, further comprising:
- a data processing system configured to be coupled with the signal active guide wire and selectively in communication with the rotary encoder and responsive to the encoder signal to produce a visual image illustrating alignment of the endovascular prosthetic device with a desired deployment location for the endovascular prosthetic device in the body of the patient.

13. The endovascular delivery system of claim 12, wherein the data processing system comprises:
- a display device;
- a memory configured to store tomography data based on an anatomy of the patient; and
- a processor in data communication with the memory and the rotary encoder, the processor operative in response to the encoder signal and data and instructions stored in the memory to produce on the display device a composite image showing an orientation of the endovascular prosthetic device relative to the anatomy of the patient.

14. The endovascular delivery system of claim 8, wherein the endovascular prosthetic devices comprises an aortic stent graft.

* * * * *